United States Patent [19]

Naegeli

[11] Patent Number: 5,107,037
[45] Date of Patent: Apr. 21, 1992

[54] PROCESS FOR THE MANUFACTURE OF α-AMBRINOL

[75] Inventor: Peter Naegeli, Wettingen, Switzerland

[73] Assignee: Givaudan Corporation, Clifton, N.J.

[21] Appl. No.: 534,108

[22] Filed: Jun. 6, 1990

[30] Foreign Application Priority Data

Jun. 13, 1989 [EP] European Pat. Off. ............ 89810451

[51] Int. Cl.$^5$ .................. C07C 35/36; C07C 29/00
[52] U.S. Cl. .................................. 568/819; 568/814; 568/816; 568/817
[58] Field of Search ................. 568/816, 817, 819, 814

[56] References Cited

U.S. PATENT DOCUMENTS 4,163,866  8/1979  Strickler ................. 568/819
4,341,908  7/1982  Willis et al. ............. 568/819

FOREIGN PATENT DOCUMENTS 0406572  1/1991  European Pat. Off. ............ 568/819
2733928  2/1978  Fed. Rep. of Germany ...... 568/819
794417   5/1958  United Kingdom ................ 568/819

OTHER PUBLICATIONS

E. T. Theimer, Ed., "Fragrance Chemistry, The Science of the Sense of Smell", Acad. Press., N.Y., 1982, pp. 551–554.
G. Ohloff, Chemie in unserer Zeit 5, (1971), pp. 114–124.
G. Buchi et al., J. Am. Chem. Soc., 78, (1956), pp. 2622–2625.

Primary Examiner—Werren B. Lone
Attorney, Agent, or Firm—Robert F. Tavares; Linda A. Vag

[57] ABSTRACT

The invention concerns a novel process for the manufacture of 2-hydroxy-2,5,5-trimethyl-1,2,3,4,4a,5,6,7-octahydronaphthalene, I, commonly known as α-ambrinol.

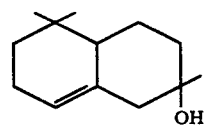

I

The process comprises reducing either an 8-halo-2-hydroxy-2,5,5-trimethyl-2,3,4,4a,5,6,7,8-octahydronaphthalene (IIa), alone or in a mixture with a 1-halo-2-hydroxy-2,5,5-trimethyl-1,2,3,4,4a,5,6,7-octahydronaphthalene (IIb), or reduced the 1,2-epoxide which can be formed therefrom, namely, 1,2-epoxy-2,5,5-trimethyl-1,2,3,4,4a,5,6,7-octanhydronaphthalene (III). The halohydrins II are prepared from 1,1,6-trimethyl-1,2,3,7,8,8a-hexahydronaphthalene, IV.

The compounds of formulas II and III are novel and form part of the present invention. The formula III epoxide possesses valuable odorant properties and its use as an odorant also forms part of the invention.

7 Claims, No Drawings

PROCESS FOR THE MANUFACTURE OF α-AMBRINOL

SUMMARY OF THE INVENTION

The invention concerns a novel process for the manufacture of 2-hydroxy-2,5,5-trimethyl-1,2,3,4,4a,5,6,7-octahydronaphthalene, I, commonly known as α-ambrinol.

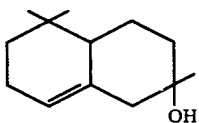

The process comprises reducing either an 8-halo-2-hydroxy-2,5,5-trimethyl-2,3,4,4a,5,6,7,8-octahydronaphihalene (IIa), alone or in admixture with a 1-halo-2-hydroxy-2,5,5-trimethyl-1,2,3,4,4a,5,6,7-octahydronaphthalene (IIb), or reducing the 1,2-epoxide which can be formed therefrom, namely, 1,2-epoxy-2,5,5-trimethyl-1,2,3,4,4a,5,6,7-octahydronaphthalene (III). The halohydrins II are prepared from 1,1,6-trimethyl-1,2,3,7,8,8a-hexahydronaphthalene, IV. This process can be illustrated as follows:

A. Formation of halohydrins from 1,1,6-trimethyl-1,2,3,7,8,8a-hexahydronaphthalene:

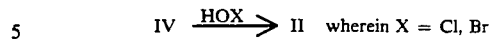

Methodology: similar to methods known per se for halohydrin formation from unsaturated hydrocarbons, namely using hypohalites, such as NaOX, Ca(OX)$_2$ (e.g. Javelle water, chloride of lime) etc. and acidic compounds such as organic or inorganic acids or their acidic salts;

Medium: organic/aqueous phase (ethers such as THF, dioxane, glycol ether, polyethylene glycol ether, or tert.alcohols, such as tert.butanol); pH 2-7, preferably about 5-6, preferably buffered;

Temperature: −10° to +35° C., especially about 5° to about 15° C.;

Work-up: conventional work-up, such as extraction with (chlorinated) hydrocarbons, ethers, esters, etc.

The separation of the 1,4- and the 1,2-halohydrins (IIa-/IIb) is not necessary, but possible, e.g. by chromatography such as adsorption chromatography. The isomers IIa and IIb are obtained in a ratio wherein IIa>IIb.

B. Epoxidation of halohydrin: II→III

Methodology: similar to methods known per se for

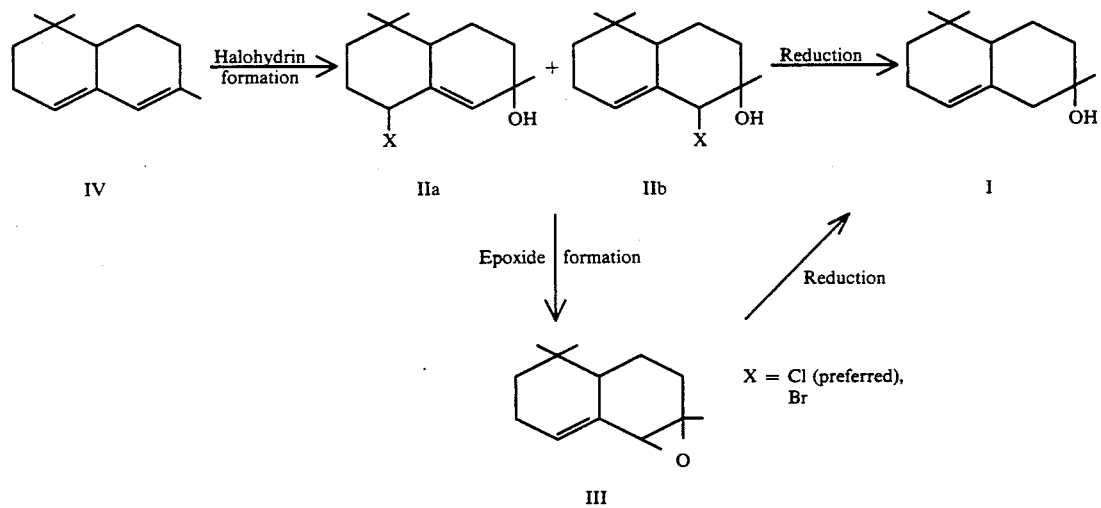

Formulas I, II, III and IV are intended to embrace all stereoisomers which occur by virtue of the asymmetric centers, formula IV having one asymmetric center, formulas IIa, IIb and III having three asymmetric centers and formula I having two asymmetric centers. Formula I is intended to embrace racemic α-ambrinol as well as racemic epi α-ambrinol and their optically active enantiomers.

The compounds of formulas II and III are novel and form part of the present invention. The formula III epoxide possesses valuable odorant properties and its use as an odorant also forms part of the invention. Compound IV is known.

DESCRIPTION OF THE PREFERRED EMBODIMENTS

The suitable parameters for the novel process are the following:

the formation of epoxides from halohydrins: there are thus suitable alkali amides such as lithium diisopropylamide, lithium dicyclohexylamide, sodium amide, etc. alkali hydrides, alkali t-butanolates, alkali t-amylates, dimethyl sulphoxide anion, alkali hydroxides/phase transfer;

Medium: anhydrous in ethers, aliphatic or aromatic hydrocarbons, tert. alcohols, etc.; or in two phases with phase transfer catalysts such as e.g. quaternary ammonium and phosphonium compounds, crown ethers, cryptates or glycol ethers or aminoglycol ethers;

Temperature: about −20° to about 120° C., preferably about 10° to about 80° C.;

Work-up: extraction with (halogenated) hydrocarbons, ethers, etc.

C. Reduction of halohydrin or epoxide: II→I or III→I

Methodology: similar to methods known per se for the reduction of halohydrins, epoxides or of allyl halides, there are thus suitable: complex hydrides, e.g. LiAlH$_4$, LiAl(OR)$_x$H$_{4-x}$, LiBR$_3$H, NaAlR$_x$H$_{4-x}$, NaAl(OR)$_x$H$_{4-x}$, (R=lower-alkyl, especially C$_{1-6}$-alkyl, preferably ethyl, and x=1,2,3), e.g. "Redal", "Vitride";

Medium: choice of the solvent and of the temperature range is especially dependent on the reducing agent; ethereal solvents or hydrocarbons are especially suitable;

Temperature: II→I about −30° C. to about 100° C., esp. about 0° C. to about 80° C., III→I about −30° C. to about 100° C., esp. about 0° C. to about 80° C.;

Work-up: hydrolysis of the intermediately-formed alcoholate, extraction with (halogenated) hydrocarbons, ethers, esters, etc;

Enrichment of the desired product can be effected by adsorption chromatography or fractional distillation.

Several syntheses for the manufacture of ambrinol are known, such as (a) Strickler, DT-OS 2733928 wherein β-ionone is used as the starting material or (b) Willis et al., U.S. Pat. No. 4,341,903 where α-ionone or α-dihydroionone is used as the starting material.

The present synthesis is technologically simple. It avoids high temperature gas phase reactions as well as a costly fractionation procedure (for the undesired educt) as in (a) above, or solid-state chemistry (Zn+H$_3$PO$_3$) as in (b). Moreover, the α-ambrinol, which is obtained from the novel process, can be used directly for perfumery. The byproducts which occur do not interfere organoleptically.

The novel epoxide III has been found to possess valuable odorant properties which make it particularly useful in fragrance compositions. The olfactory notes of III can be characterized as follows: faecal, fecal or animal, after perspiration, urine of wildcats. These notes are surprising, because closely related epoxides such as those taught by E. T. Theimer, Fragrance Chemistry, Acad. Press 1982, pp. 552, 553, 554 and G. Ohloff, Chemie in unserer Zeit 5, 114 (1971) would give rise to the expectation of an ambrox odour (=ambroxane: warm, tobacco-like) and woody odour (sandalwood). These notes are, however, absent. Also, the sidenotes—namely eucalyptus and camphor—which are referred to in the art are missing completely.

On the basis of its olfactory notes the epoxide of formula III is especially suitable for modifying and intensifying known compositions. In particular, its extraordinary olfactory strength, which contributes quite generally to the refinement of the compositions, should be emphasized.

The epoxide III combines with numerous known odorant ingredients of natural or synthetic origin, whereby the range of the natural odorants can embrace not only readily-volatile, but also moderately-volatile and difficultly-volatile components, and that of the synthetics can embrace representatives from practically all classes of substances, as will be evident from the following compilation:

Natural products, such as tree moss absolute, basil oil, tropical fruit oils (such as bergamot oil, mandarin oil, etc.), mastix absolute, myrtle oil, palmarosa oil, patchouli oil, petitgrain oil, Paraguay, wormwood oil, alcohols, such as farnesol, geraniol, linalool, nerol, phenylethyl alcohol, rhodinol, cinnamic alcohol, Sandalore ® (Givaudan) (3-methyl-5-(2,2,3-trimethylcyclopent-3-en-1-yl)pentan-2-ol), Sandela ® (Givaudan) (3-isocamphyl-(5)-cyclohexanol), aldehydes, such as citral, α-methyl-3,4-methylenedioxyhydrocinnamic aldehyde, α-hexylcinnamaldehyde, hydroxycitronellal, Lilial ® (Givaudan) (p-tert.butyl-α-methyldihydrocinnamaldehyde), methylnonylacetaldehyde, ketones, such as allylionone, α-ionone, β-ionone, isoraldein (isomethyl-α-ionone), methylionone, esters, such as allyl phenoxyacetate, benzyl salicylate, cinnamyl propionate, citronellyl acetate, citronellyl ethoxolate (citronellyl.O—CO—CO.OC$_2$H$_5$), decyl acetate, dimethylbenzylcarbinyl acetate, dimethylbenzylcarbinyl butyrate, ethyl acetoacetate, ethyl acetylacetate, hexenyl isobutyrate, linalyl acetate, methyl dihydrojasmonate, styrallyl acetate, vetiveryl acetate, 2-ethyl-6,6-dimethyl (and 2,3,6,6-tetramethyl)-2-cyclohexene-1-carboxylic acid ethyl ester, trichloromethylbenzyl acetate, Vetynal ® (Givaudan) (acetylated caryophyllene), lactones, such as γ-undecalactone, various components often used in perfumery, such as musk ketone, indole, p-menthane-8-thiol-3-one, methyleugenol.

Further, the manner in which III rounds-off and harmonizes the olfactory notes of a wide range of known compositions without, however, dominating in an unpleasant manner is remarkable. There are to be mentioned in this connection: compositions with flowery, e.g. jasmine or rose, notes as well as woody, chypre, animalic, tobacco-like and patchouli compositions, etc.

The epoxide of formula III can be used in wide limits which can extend in compositions, for example, from about 0.1 (detergents)—about 5% (alcoholic solutions), without these values being, however, limiting values, since the experienced perfumer can also achieve effects with even lower concentrations or can synthesize novel complexes with even higher amounts. The preferred concentrations range between about 0.1% and about 3%. The compositions manufactured with III can be used for all kinds of perfumed consumer goods (eau de cologne, eau de toilette, extracts, lotions, creams, shampoos, soaps, salves, powders, toothpastes, mouth washes, deodorants, detergents, tobacco, etc.).

The epoxide III can accordingly be used in the manufacture of compositions and, as the above compilation shows, a wide range of known odorants or odorant mixtures can be used. In the manufacture of such compositions the known odorants enumerated above can be used according to methods known to the perfumer, such as e.g. from W. A. Poucher, Perfumes, Cosmetics and Soaps 2, 7th edition, Chapman and Hall, London, 1974.

ILLUSTRATION OF THE PREFERRED EMBODIMENTS

EXAMPLE 1

1,1,6-Trimethyl-1,2,3,7,8,8a-hexahydronaphthalene, IV, 89% (26.45 g 150 mmol) is dissolved in 250 ml of THF and treated with a solution of 47.63 g (350 mmol) of KH$_2$PO$_4$ in 350 ml of water. The white suspension is cooled in an ice bath and there are thereafter added dropwise within one hour at 4°–8° C., 106 ml (155 mmol) of NaOCl solution (11%), then at ~5° C. a further 10 ml (15 mmol) of the NaOCl solution and, after a total of 2.5 hours, the mixture is worked-up. The reaction mixture is extracted four times with 100 ml of ether each time, the entire organic phase is washed with 100 ml of water and this aqueous phase is again extracted with 50 ml of ether. The organic phase is dried over MgSO$_4$, filtered off and evaporated in a rotary evaporator. There are obtained 36.19 g of a pale yellow liquid of IIa+IIb which can be used without further purification. The main product IIa, which can be separated by low-pressure column chromatography on silica gel, exhibits the following physical data:

IR (film): 3350, 1450, 1385, 1365, 1223, 1190, 1160, 1150, 1120, 1030, 990, 902, 857, 706, 635 cm$^{-1}$. H-NMR (400 MHz, CDCl$_3$, decoupling, NOE) [nuclear Overhouser effect]: 5.77 ppm (1H, narrow triplet); 4.68 ppm (1H, narrow multiplet); 2.33 ppm (1H, split double doublet); 1.295 and 1.03 and 0.782 ppm (in each case 3H singlet for angular methyl groups).

EXAMPLE 2

Redal (NaAl(OCH$_2$CH$_2$OCH$_3$)$_2$H$_2$), 70%, (60.85 g, 210.6 mmol) is placed in 190 ml of toluene. Compound II (24.10 g, 105.3 mmol) (crude product) from 70% IV, in 190 ml of toluene is added dropwise at 23°-33° C. during 80 minutes. The slightly turbid mixture is stirred at 55° C. for a further 3.5 hours, hydrolyzed in an ice bath with water and worked-up as follows: the organic phase is washed four times with 80 ml of water each time, the entire aqueous phase is extracted three times with 70 ml of hexane each time and the hexane phase is washed neutral with water. The combined organic phases are dried over MgSO$_4$ and evaporated. There are obtained 19.58 g of a pale yellow liquid. The crude product is held at reflux temperature for 2.5 hours with 35 ml of 5N KOH in 200 ml of isopropanol. Thereafter, the mixture is diluted with 100 ml of water and 100 ml of hexane, the phases are separated, the aqueous phase is extracted three times with 100 ml of hexane each time, the combined organic phases are washed neutral with water and the wash-water is agin extracted with hexane. The organic phase is dried over MgSO$_4$, filtered off and evaporated. There result 16.37 g of a yellow liquid (54% α-ambrinol). The crude product is separated from the top fraction and residue by bulb-tube distillation (0.08 Torr/60°-80°). There result 9.33 g of slightly yellowish liquid with the typical strong animalic, earthy-camphorous and musk-like α-ambrinol odour (content of α-ambrinol 58%; content of epi-α-ambrinol:17%). The enrichment of the α-ambrinol can be effected by fractional distillation or by chromatography.

EXAMPLE 3

Lithium aluminium hydride (5.95 g, 156.9 mmol) in 250 ml of ether is placed in an apparatus which has been pre-flushed with nitrogen. Compound II (35.90 g, 156.9 mmol) (crude product) in 250 ml of ether is added dropwise at 24°-30° C. within 1 hour. The mixture is back-washed with 30 ml of ether and the grey suspension is held at reflux temperature for 2 hours. Thereafter, the mixture is hydrolyzed with 200 ml of saturated potash solution, then worked-up as follows: the organic phase is washed three times with 50 ml of water each time, the combined aqueous phases are extracted four times with 100 ml of ether each time and this ether phase is washed four times with 50 ml of water each time until neutral. The ether phases are combined, dried over MgSO$_4$, filtered off and evaporated. There result 28.52 g of a yellow liquid. The crude product, α-ambrinol, is held at reflux temperature for a total of 4 hours with 100 ml of 2N KOH in ethanol. The brown solution is thereafter diluted with 100 ml of water, extracted eight times with 50 ml of hexane each time, the organic phase is washed neutral with water, dried over MgSO$_4$, filtered off and evaporated. The crude product (19.67 g) is held at reflux temperature for 2 hours with KOH/EtOH, worked-up and fractionated over a 2 cm Vigreux column at 0.08 Torr. The α-ambrinol obtained is 50%.

EXAMPLE 4

Sodium hydride (55%) (9.57 g, 219.1 mmol) is placed in 360 ml of THF and 41.76 g (182.6 mmol) of compound II (crude product) in 360 ml of THF is added dropwise at 21°-25° C. during 1.5 hours. The grey suspension becomes mustard-yellow. It is stirred at 40° C. for a further 4 hours, hydrolyzed in an ice bath with saturated potash solution and worked-up. The aqueous phase is extracted four times with 120 ml of ether each time, the entire organic phase is washed four times with 100 ml of water each time and the aqueous phase is extracted twice with 100 ml of ether each time. The combined organic phases are dried over MgSO$_4$, filtered off and evaporated. There remain 31.79 g of a liquid which is held at reflux temperature for 2½ hours with 50 ml of 5N KOH in 300 ml of isopropanol. Thereafter, the mixture is diluted with water and extracted with hexane. The organic phase is washed with water until neutral, dried over MgSO$_4$, filtered off and evaporated. There result 27.67 g of a dark yellow liquid which are separated from the residue by bulb-tube distillation at 0.08 Torr and 60°-80° C. Yield: 18.12 g (66% of α-and 12.5% of β-epoxide). A sample purified by chromatography on silica gel exhibits the following physical data for III:

GC: 90-91%, 72% α-epoxide+18% β-epoxide.

IR (film): 1660, 1450, 1382, 1360, 1298, 1288, 1217, 1191, 1018, 1005, 948, 925, 872, 840/830/820, 775, 745, 692, 660 cm$^{-1}$. H-NMR (400 MHz, CDCl$_3$): (for the main product=α-epoxide): 5.865 ppm (1H, narrow multiplet); 3.163 ppm (1H, singlet), 1.352 ppm (3H, singlet); 0.928 ppm (3H, singlet); 0.748 ppm (3H, singlet): (minor product=β-epoxide): 5.92 ppm (1H, narrow multiplet); 3.185 ppm (1H, singlet); 1.352 ppm (3H, singlet); 0.928 ppm (3H, singlet); 0.71 ppm (3H, singlet). In C$_6$D$_6$ the three singlets for each of the three angular methyl groups are separated visibly.

MS: main product: M$^+$=192(12); m/e=177(5), 176(7), 163(3), 161(9), 159(4), 150(37), 135(20), 121(17), 107(44), 94(100), 79(39), 67(15), 55(21), 43(64). By-product: M$^+$=192(13); m/e=177(5), 176(3), 163(3), 161(3), 159(4), 150(30), 135(18), 121(19), 107(47), 94(100), 79(48), 67(18), 55(22), 43(72). Odour: faecalic, animalic, perspiration of wildcat.

EXAMPLE 5

Lithium aluminium hydride (0.10 g 2.6 mmol) is placed in 10 ml of ether and 0.50 g (2.6 mmol) of compound III in 10 ml of ether is added. Thereafter, the mixture is held at reflux for 1.5 hours, hydrolyzed in an ice bath with saturated potash solution and worked-up. The organic phase is washed with water and the entire aqueous phase is extracted with ether. The combined organic phases are dried over MgSO$_4$, filtered off and evaporated on a rotary evaporator. There results 0.53 g of a colourless liquid with the strong camphorous-indolic-animalic odour of α-ambrinol. According to the gas chromatogram, the product contains 76% of α-ambrinol and 13% of epi-α-ambrinol.

EXAMPLE 6

| a) Patchouli note | Compositions Parts by weight | |
|---|---|---|
| α-Hexylcinnamaldehyde | 30 | |
| Vanillin | 10 | |
| Sandela ® (Givaudan) (3-isocamphyl-(5)-cyclohexanol) | 10 | |
| Lilial ® (Givaudan) (p-tert.butyl-α-methyl-dihydrocinnamaldehyde) | 40 | |
| Indole (2,3-benzpyrrole) 10% in DPG | 2 | |
| Coumarin | 25 | |
| Fixolide ® (Givaudan) (7-acetyl 1,1,3,4,4,6,-hexamethyltetralin) | 5 | |
| Isoeugenol | 7 | |
| Peche pure (γ-undecalactone) | 2 | |
| Veiynal ® (Givaudan) (acetylated caryophyllene) | 30 | |
| Eugenol | 50 | |
| *Cannelier feuilles* ess. rest. (cinnamon leaf oil) | 15 | |
| Patchouli essence | 90 | |
| Hydroxycitronellal | 40 | |
| β-Phenylethyl alcohol | 100 | |
| Geraniol | 30 | |
| Benzyl acetate | 35 | |
| Linalyl acetate | 40 | |
| Omega-n-undecylene aldehyde | 3 | |
| Linalool | 30 | |
| DPG | 406 | 401 |
| Compound III | — | 5 |
| | 1000 | 1000 |

The original composition gains in volume and strength by the addition of compound III. The animalic and patchouli notes are intensified.

| b) Rose note | Parts by weight | |
|---|---|---|
| Geraniol | 120 | |
| Citronellol | 60 | |
| Rhodinol | 100 | |
| Phenylethyl alcohol | 580 | |
| Linalool | 20 | |
| Trichloromethylbenzyl acetate | 50 | |
| Acetate DMBC (dimethylbenzylcarbinyl acetate) | 30 | |
| DPG | 40 | 37 |
| Compound III | — | 3 |
| | 1000 | 1000 |

The original composition gains in volume and strength by the addition of compound III and a pleasant intensification and fixing of the woody note takes place. At the same time, the composition gains in density.

I claim:

1. A process for the manufacture of 2-hydroxy-2,5,5-trimethyl-1,2,3,4,4a,5,6,7-octahydronaphthalene of the formula

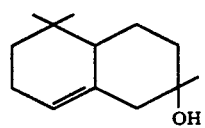

I which comprises reducing a 8-halo-2-hydroxy-2,5,5-trimethyl-2,3,4,4a,5,6,7,8-octahydronaphthalene of the formula

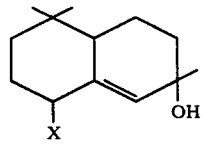

IIa or a mixture of said 8-halo-2-hydroxy-2,5,5-trimethyl-2,3,4,4a,5,6,7,8-octahydronaphthalene in admixture with a 1-halo-2-hydroxy-2,5,5-trimethyl-1,2,3,4,4a,5,6,7-octahydronaphthalene of the formula

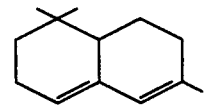

IIb wherein X is chloro or bromo, in the presence of a complex hydride as the reducing agent and at a temperature from about −30° C. to about 100° C.

2. A process according to claim 1 wherein the formula IIa compound and the formula IIb compound are prepared from 1,1,6-trimethyl-1,2,3,7,8,8a-hexahydronaphthalene of the formula

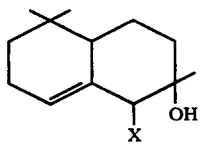

IV

3. A process according to claim 2 wherein
a) X is chloro, and,
b) the complex hydride is selected from the group consisting of LiAlH$_4$, LiAl(OR)$_x$H$_{4-x}$, LiBR$_3$H, NaAlR$_x$H$_{4-x}$, NaAl(OR)$_x$H$_{4-x}$ wherein R represents lower alkyl and x is 1, 2 or 3.

4. A process for the manufacture of 2-hydroxy-2,5,5-trimethyl-1,2,3,4,4a,5,6,7-octahydronaphthalene of the formula

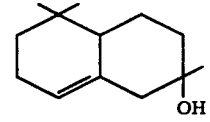

I which comprises reducing 1,2-epoxy-2,5,5-trimethyl-1,2,3,4,4a,5,6,7-octahydronaphthalene of the formula

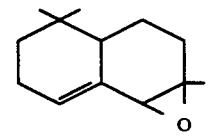

III in the presence of a complex hydride as the reducing agent and at a temperature from about −30° C. to about 100° C.

5. A process according to claim 4 wherein the compound of formula III is prepared from 8-halo-2-hydroxy-2,5,5,-trimethyl-2,3,4,4,4a,5,6,7,8-octahydronaphthalene of the formula

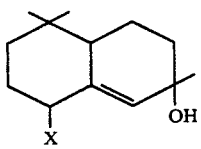

or a mixture of said 8-halo-2-hydroxy-2,5,5-trimethyl-2,3,4,4a,5,6,7,8-octahydronaphthalene in admixture with a 1-halo-2-hydroxy-2,5,5,-trimethyl-2,3,4,4a,5,6,7,8-octahydronaphthalene of the formula

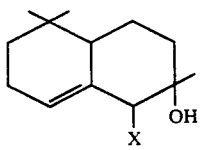

IIb wherein X is chloro or bromo.

6. A process according to claim 5 wherein the formula IIa compound and the formula IIb compound are prepared from 1,1,6-trimethyl-1,2,3,7,8,8a-hexahydronaphthalene of the formula

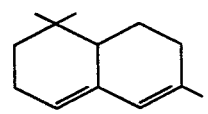

IV

7. A process according to claim 6 wherein
a) X is chloro, and
b) the complex hydride is selected from the group consisting of LiAlH$_4$, LiAl(OR)$_x$H$_{4-x}$, LiBR$_3$H, NaAlR$_x$H$_{4-x}$ NaAl(OR)$_x$H$_{4-x}$ wherein R represents lower alkyl and x is 1, 2 or 3.

* * * * *